United States Patent
Michal et al.

(10) Patent No.: US 8,067,023 B2
(45) Date of Patent: *Nov. 29, 2011

(54) IMPLANTABLE MEDICAL DEVICES INCORPORATING PLASMA POLYMERIZED FILM LAYERS AND CHARGED AMINO ACIDS

(75) Inventors: Eugene T. Michal, San Francisco, CA (US); Charles D. Claude, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1608 days.

This patent is subject to a terminal disclaimer.

(21) Appl. No.: 11/183,030

(22) Filed: Jul. 15, 2005

(65) Prior Publication Data
US 2005/0249777 A1    Nov. 10, 2005

Related U.S. Application Data

(62) Division of application No. 10/176,506, filed on Jun. 21, 2002, now Pat. No. 7,056,523.

(51) Int. Cl.
*A61F 2/02* (2006.01)
(52) U.S. Cl. .................................... 424/423
(58) Field of Classification Search .................. None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,835,175 A | 9/1974 | Carpino et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,908,404 A | 3/1990 | Benedict et al. |
| 4,917,309 A | 4/1990 | Zander et al. |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,025,001 A | 6/1991 | Loscalzo et al. |
| 5,100,992 A | 3/1992 | Cohn et al. |
| 5,112,457 A | 5/1992 | Marchant |
| 5,133,742 A | 7/1992 | Pinchuk |
| 5,155,137 A | 10/1992 | Keefer et al. |
| 5,163,952 A | 11/1992 | Froix |
| 5,165,919 A | 11/1992 | Sasaki et al. |
| 5,187,183 A | 2/1993 | Loscalzo et al. |
| 5,202,129 A | 4/1993 | Samejima et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,356,890 A | 10/1994 | Loscalzo et al. |
| 5,366,997 A | 11/1994 | Keefer et al. |
| 5,380,299 A | 1/1995 | Fearnot et al. |
| 5,405,919 A | 4/1995 | Keefer et al. |
| 5,417,981 A | 5/1995 | Endo et al. |
| 5,424,077 A | 6/1995 | Lajoie |
| 5,428,070 A | 6/1995 | Cooke et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,482,720 A | 1/1996 | Murphy et al. |
| 5,485,496 A | 1/1996 | Lee et al. |
| 5,516,881 A | 5/1996 | Lee et al. |
| 5,536,723 A | 7/1996 | Loscalzo et al. |
| 5,543,099 A | 8/1996 | Zhang et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |

(Continued)

FOREIGN PATENT DOCUMENTS

DE    42 24 401    1/1994

(Continued)

OTHER PUBLICATIONS

U.S. Appl. No. 10/177,156, filed Jun. 21, 2002, Michal et al.
U.S. Appl. No. 10/176,499, filed Jun. 21, 2002, Hossainy et al.
U.S. Appl. No. 10/177,114, filed Jun. 21, 2002, Simhambhatla et al.
U.S. Appl. No. 10/177,942, filed Jun. 21, 2002, Michal et al.
U.S. Appl. No. 10/176,506, filed Jun. 21, 2002, Claude et al.
U.S. Appl. No. 10/177,117, filed Jun. 21, 2002, Hossainy et al.
U.S. Appl. No. 10/320,899, filed Dec. 16, 2002, Shah et al.
Anonymous, Reducing the pH of a peptide oligomer to prepare for systemic delivery, Defensive Publication, Research Disclosure, p. 905 (Aug. 2003).
Anonymous, *Cardiologists Draw-Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

(Continued)

*Primary Examiner* — Carlos Azpuru
(74) *Attorney, Agent, or Firm* — Squire Sanders & Dempsey, (US)LLP

(57) ABSTRACT

An implantable medical device, such as a stent, is disclosed comprising an amino acid or a polypeptide bonded to a plasma polymerized film layer formed on the device. A method of manufacturing the same is also disclosed.

13 Claims, No Drawings

U.S. PATENT DOCUMENTS

| | | | |
|---|---|---|---|
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,639,441 A | 6/1997 | Sievers et al. |
| 5,644,020 A | 7/1997 | Timmermann et al. |
| 5,649,977 A | 7/1997 | Campbell |
| 5,650,442 A | 7/1997 | Mitchell et al. |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,804,318 A | 9/1998 | Pinchuk et al. |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,852,058 A | 12/1998 | Cooke et al. |
| 5,854,376 A | 12/1998 | Higashi |
| 5,858,746 A | 1/1999 | Hubbell et al. |
| 5,861,168 A * | 1/1999 | Cooke et al. ................. 424/424 |
| 5,865,814 A | 2/1999 | Tuch |
| 5,869,127 A | 2/1999 | Zhong |
| 5,873,904 A | 2/1999 | Ragheb et al. |
| 5,874,165 A | 2/1999 | Drumheller |
| 5,876,433 A | 3/1999 | Lunn |
| 5,877,224 A | 3/1999 | Brocchini et al. |
| 5,879,713 A | 3/1999 | Roth et al. |
| 5,891,459 A | 4/1999 | Cooke et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,945,452 A | 8/1999 | Cooke et al. |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,060,534 A | 5/2000 | Ronan et al. |
| 6,063,432 A | 5/2000 | Maxwell et al. |
| 6,077,543 A | 6/2000 | Gordon et al. |
| 6,080,488 A | 6/2000 | Hostettler et al. |
| 6,095,134 A | 8/2000 | Sievers et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,117,872 A | 9/2000 | Maxwell et al. |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,183,783 B1 | 2/2001 | Benoit et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,228,346 B1 | 5/2001 | Zhang et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,166 B1 | 10/2001 | Barry et al. |
| 6,306,176 B1 | 10/2001 | Whitbourne |
| 6,306,993 B1 | 10/2001 | Rothbard et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |

| | | |
|---|---|---|
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,481 B1 * | 6/2004 | Larik et al. .................. 623/1.45 |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,994,867 B1 * | 2/2006 | Hossainy et al. ............. 424/423 |
| 7,033,602 B1 * | 4/2006 | Pacetti et al. ................ 424/426 |
| 7,056,523 B1 * | 6/2006 | Claude et al. ................ 424/426 |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |

| | | |
|---|---|---|
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/082368 | 10/2003 |
| WO | WO 63/080147 | 10/2003 |
| WO | WO 04/000383 | 12/2003 |
| WO | WO 2004/009145 | 1/2004 |

OTHER PUBLICATIONS

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752 printed Aug. 25, 2003 (2 pages).

Anderson et al., *Nitric-Oxide and Nitrovasodilators: Similarities, Differences and Potential Interactions*, JACC 24(2):555-566 (1994).

Anderson et al., *Close Relation of Endothelial Function in the Human Coronary and Peripheral Circulations*, JACC 26(5):1235-1241 (1995).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Bode-Boger et al., *Elevated L-Arginine/Dimethylarginine Ratio Contributes to Enhanced Systemic NO Production by Dietary L-Arginine in Hypercholesterolemic Rabbits*, Biochem. and Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al., *Asymmetric Dimethylarginine: A Novel Risk Factor for Endothelial Dysfunction*, Circ. 96(8):1-32 (1997).

Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).

Candipan et al., *Regression or Progression: Dependency on Vascular Nitric Oxide*, Arterioscler. Thromb. Vasc. Biol. 16(1):44-50 (1996).

Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).

Cooke et al., *Arginine: A New Therapy for Atherosclerosis?* Circ. 95(2):311-312 (1997).

Cooke et al., *Cytoprotective Effects of Nitric Oxide*, Circ. 88(5)1:2451-2454 (1993).

Cooke et al., *Derangements of the Nitric Oxide Synthase Pathway, L-Arginine, and Cardiovascular Diseases*, Circ. 96(2):379-382 (1997).

Cooke et al., *Diffuse Coronary Artery Disease and Endothelial Dysfunction: Form Follows Function*, ACC Curr. J. Rev. pp. 19-25 (Nov./Dec. 2000).

Cooke et al., *Regression and Progression: Dependency Upon NO* (Abstract), J. Investi. Med. 43(2) Suppl. 2:211A (1995).

Cooke et al., *The Role of Endothelium-Derived Nitric Oxide in Atherosclerosis*, Adv. Vasc. Path. 1150:3-14 (1997).

Cooke, *Does ADMA Cause Endothelial Dysfunction?*, Arterioscler. Thromb. Vasc. Biol. 20:2032-2037 (2002).

Cooke, *Enhancement of Endogenous Vascular Nitric Oxide: A New Therapeutic Strategy for Restenosis* (Abstract 301), Eur. J. Clin. Investi. 28:A53 (1998).

Cooke, *Is Atherosclerosis an Arginine Deficiency Disease?*, J. Investi. Med. 46(8):377-380 (1998).

Cooke, *Nutriceuticals for Cardiovascular Health*, Am. J. Cardio., 82(10A):43S-46S (1998).

Cooke, *Role of Nitric Oxide in Progression and Regression of Atherosclerosis*, West. J. Med. 164(5):419-424 (1996).

Cooke, *The 1998 Nobel Prize in Medicine: Clinical Implications for 1999 and Beyond*, Vasc. Med. 4:57-60 (1999).

Cooke, *The Endothelium: A New Target for Therapy*, Vasc. Med. 5:49-43 (2000).

Cooke, *The Pathophysiology of Peripheral Arterial Disease: Rational Targets for Drug Intervention*, Vasc. Med. 2:227-230 (1997).

Creager et al., *L-Arginine Improves Endothelium-Dependent Vasodilation in Hypercholesterolemic Humans*, J. Clin. Investi. 90:1248-1253 (1992).

Drexler et al., *Effect of L-Arginine on Coronary Endothelial Function in Cardiac Transplant Recipients: Relation to Vessel Wall Morphology*, Circ. 89(4):1615-1623 (1994).

Drexler et al., *Endothelial Dysfunction in the Coronary Circulation After Cardiac Transplantation: Effect of L-Arginine* (Abstract I356), Circ. 86(4) Supp:1418 (1992).

Dulak et al., *Nitric Oxide Induces the Synthesis of Vascular Endothelial Growth Factor by Rat Vascular Smooth Muscle Cells*, Arterioscler. Thromb. Vasc. Biol. 20:659-666 (2002).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

http://www.lf2.cuni.dz/physiolres/1997/issue5/iss5cl6.html,
Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).
Gaiser et al., *Lethal Short-Limbed Dwarfism in Transgenic Mice with an Arginine to Cysteine Substitution in Alpha-I (II) Procollagen* (Abstract 3369), Mol. Biol. Cell 7:579A (1996).
Ganz et al., *Coronary Vasospasm in Humans—The Role of Atherosclerosis and of Impaired Endothelial Vasodilator Function*, Basic Res. Cardiol. 86(Suppl 2):215-222 (1991).
Gregory et al., *Enhanced Nitric Oxide Production Induced by the Administration of L-Arginine Does Not Inhibit Arterial Neointimal Formation After Overwhelming Alloimmune Injury*, J. Heart Lung Transplant. 15(1)Part 1:58-66 (1996).
Gregory et al., *Nitric Oxide Induced by the Administration of L-Arginine Does Not Inhibit Arterial Neointimal Formation Following Alloimmune Injury* (Abstract 41), J. Heart Lung Transplant. 14(1)Part 2:S45 (1995).
Helmus, *Overview of Biomedical Materials*, MRS Bulletin, pp. 33-38 (Sep. 1991).
Heeschen et al., *Hypercholesterolemia Impairs Angiogenic Response to Hind Limb Ischemia: Role of ADMA* (Abstract 2490), Circ. I-473 (1999).
Herdeg et al., *Antiproliferative Stent Coatings: Taxol and Related Compounds*, Semin. Intervent. Cardiol. 3:197-199 (1998).
Ho et al., *Dietary L-Arginine Reverses the Inhibitory Effect of Asymmetric Dimethylarginine on Angiogenesis in Hypercholesterolemia* (Abstract 407-2), JACC 33:1A (1999).
Huang et al., *Biodegradable Polymers Derived from Aminoacids*, Macromol. Symp. 144, 7-32 (1999).
Huet et al., *Structural Homologies Between Two HLA B27-Restricted Peptides Suggest Residues Important for Interaction with HLA B27*, Intl. Immunol. 2(4):311-316 (1990).
Hutchison et al., *Effects of L-Arginine on Atherogenesis and Endothelial Dysfunction Due to Secondhand Smoke*, Hyperten. 34:44-50 (1999).
Inoue et al., *An AB block copolymer of oligo(methyl methacrylate) and poly(acrylic acid) for micellar delivery of hydrophobic drugs*, Journal of Controlled Release 51:221-229 (1998).
Jang et al., *Angiogenesis is Impaired by Hypercholesterolemia: Role of Asymmetric Dimethylarginine*, Circ. 102:1414-1419 (2000).
Jang et al., *L-Arginine Reverses the Anti-Angiogenic Effects of Asymmetric Dimethylarginine* (Abstract), J. Investi. Med. 4(2):86A (1999).
Jozkowicz et al., *Genetic Augmentation of Nitric Oxide Synthase Increases the Vascular Generation of VEGF*, Cardiovasc. Res. 51:773-783 (2001).
Kataoka et al., *Block copolymer micelles as vehicles for drug delivery* Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Kown et al., *Arginine Polymers Inhibit Graft Coronary Artery Disease Following Cardiac Transplantation* (Abstract 726), Transplant. 69(8):S300 (2000).
Kown et al., *L-Arginine Polymers Inhibit the Development of Vein Graft Neointimal Hyperplasia*, J. Thorac. Cardiovasc. Surg. 121(5):971-980 (2001).
Kown et al., *L-Arginine Polymer Mediated Inhibition of Graft Coronary Artery Disease After Cardiac Transplantation*, Transplant. 71(11):1542-1548 (2001).
Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).
Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).
Kyte et al., *A Simple Method for Displaying the Hydropathic Character of a Protein*, J. Mol. Biol. 157:105-132 (1982).

Latron et al., *Positioning of a Peptide in the Cleft of HLA-A2 by Complementing Amino Acid Changes*, PNAS 88:11325-11329 (1991).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Lieberman et al., *Estrogen Improves Endothelium-Dependent, Flow-Mediated Vasodilation in Postmenopausal Women*, Annals Intern. Med. 121(12):936-941 (1994).
Lieberman et al., *Flow-Induced Vasodilation of the Human Brachial Artery is Impaired in Patients <40 Years of Age with Coronary Artery Disease*, Am. J. Cardiol. 78:1210-1214 (1996).
Lim et al., *Acute Local Delivery of L-Arginine Reduces Long Term Intimal Thickening and Macrophage Infiltration* (Abstract 2346), Circ. 94(8):I403 (1996).
Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).
Lissin et al., *Maintaining the Endothelium: Preventive Strategies for Vessel Integrity*, Prev. Cardio. 3:172-177 (2000).
Liu et al., *Drug release characteristics of unimolecular polymeric micelles*, Journal of Controlled Release 68:167-174 (2000).
Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).
Maxwell et al., *A Nutritional Product Designed to Enhance Nitric Oxide Activity Restores Endothelium-Dependent Function in Hypercholesterolemia*, J. Investi. Med. 47(2):45A (1999).
Maxwell et al., *Cardiovascular Effects of L-Arginine*, Curr. Opin. Nephrol. Hyperten. 7:63-70 (1998).
Maxwell et al., *Endothelial Dysfunction in Hypercholesterolemia is Reversed by a Nutritional Product Designed to Enhance Nitric Oxide Activity*, Cardiovasc. Drugs Therapy 14:309-316 (2000).
Maxwell et al., *Improvement in Walking Distance and Quality of Life in Peripheral Arterial Disease by a Medical Food* (Abstract 86), Nitric Oxide: Biology and Chemistry, 4(3):232 (2000).
Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).
Maxwell et al., *L-Arginine Attenuates the Impairment in Exercise Capacity Due to Hypercholesterolemia* (Abstract), JACC 29:265A (1997).
Maxwell et al., *L-Arginine Enhances Aerobic Exercise Capacity in Association with Augmented Nitric Oxide production*, J. Appl. Physiol. 90:933-938 (2001).
Maxwell et al., *Limb Blood Flow During Exercise is Dependent on Nitric Oxide*, Circ. 98:369-374 (1998).
Maxwell et al., *Modulation of the Nitric Oxide Synthase Pathway in Atherosclerosis*, Exp. Physiol. 83:573-584 (1998).
Maxwell et al, *Nutritional Therapy for Peripheral Arterial Disease: A Double-Blind, Placebo-Controlled, Randomized Trial of HeartBar®*, Vasc. Med. 5:11-19 (2000).
Maxwell et al., *The Role of Nitric Oxide in Atherosclerosis*, Cor. Art. Dis. 10:277-286 (1999).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Meredith et al., *Role of Endothelium in Ischemic Coronary Syndromes*, Am. J. Cardiol. 72(8):27C-32C (1993).
Meredith et al., *Role of Impaired Endothelium-Dependent Vasodilation in Ischemic Manifestations of Coronary Artery Disease*, Circ. 87(5) Suppl:V56-V66 (1993).
Mitchell et al.; *Polyarginine Enters Cells More Efficiently than Other Polycationic Homopolymers*, J. Peptide Res. 56:318-325 (2000).
Miyazaki et al., *Endogenous Nitric Oxide Synthase Inhibitor: A Novel Marker of Atherosclerosis*, Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate in the Absence of Changes in Aterial Blood Pressure When Applied Topically to the Sino-Atrial Node in the Anaesthetized Pig*, J. Physiol. (2000), printed Jun. 12, 2001.

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study*, Lancet 353:1838-1842 (1999).

Niebauer et al., *Gene Transfer of Nitric Oxide Synthase: Effects on Endothelial Biology*, JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:I-551 (1997).

Niebauer et al., *Local L-Arginine Delivery After Balloon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Nordrehaug et al., *A novel biocompatible coating applied to coronary stents*, EPO Heart Journal 14, p. 321 (P1694), Abstr. Suppl. (1993).

Ohno et al., *Shear Stress Elevates Endothelial cGMP: Role of a Potassium Channel and G Protein Coupling*, Circ. 88:193-197 (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide*, Intl. Immunol. 1(4):487-495 (1989).

Saotome, et al., *Novel Enzymatically Degradable Polymers Comprising α-Amino Acid, 1,2-Ethanediol, and Adipic Acid*, Chemistry Letters, pp. 21-24, (1991).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain*, J. Exp. Med. 159:1351-1370 (1984).

Schwarzacher et al., *L-$N^G$-Nitro-Arginine Methyl Ester in the Anesthetized Rabbit: Venous Vasomotion and Plasma Levels*, J. Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone* in vivo *Using Intravascular Ultrasound*, J. Pharmacol, Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads to Enhanced Venous Reactivity* in vivo, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty*, Circ. 95(7):1863-1869 (1997).

Schwarzacher, *New Therapeutic Approaches for Correction of Endothelial Function After Balloon Dilatation* (Eng. Abstract), J Kardiologie 7(1):14-17 (2000).

Schwarzacher et al., *Altered Reactivity of the Inferior Vena Cava to Noradrenaline and Acetylcholine Following the Blockade of EDRF-Biosynthesis with $N^G$-Nitro-$_L$-Arginine Methyl Ester*, Clin. Exp. Pharmacol. Physiol. 23(6/7):490-492.

Selwyn et al., *Pathophysiology of Ischemia in Patients with Coronary Artery Disease*, Prog. Cardiovasc. Dis. XXXV(1):27-39 (1992).

http://www.pharmsci.org/scientificjournals/pharmsci/journal/99_7.html, Shameem et al., *A Short Term (Accelerated Release) Approach to Evaluate Peptide Release from PLGA Depot-Formulations*, Published Jul. 21, 1999, printed Feb. 19, 2002.

Shigeno, *Prevention of Cerebrovascular Spasm by Bosentan, Novel Endothelin Receptor*, Chemical Abstract 125:212307 (1996).

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract 120), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl:1942 (1992).

Singer et al., *Dietary Supplements of L-Arginine Reduce Atherogenesis and Alter Vascular Reactivity in Hypercholesterolemic Animals* (Abstract) Clin. Res. 41(1):78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).

Tangphao et al., *Diurnal Variation of Plasma L-Arginine Concentrations and the Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans is Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by The NO Precursor* (Abstract 765-4), JACC 25:276A (1995).

Todd et al., *Regulation of Loblolly Pine (Pinus taeda L.) Arginase in Developing Seedling Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enhanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines* Circ. 85(4):1390-1397 (1992).

von der Leyen et al., *Gene Therapy Inhibiting Neointimal Vascular Lesion: in vivo Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase as an in vivo Gene Transfer Approach to Prevent Neointima Formation After Vascular Injury*, Clin. Res. 42(2):180A (1994).

van Beusekom et al., *Coronary stent coatings*, Coronary Artery Disease 5(7):590-596 (Jul. 1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wilensky et al., *Methods and Devices for Local Drug Delivery in Coronary and Peripheral Arteries*, Trends Cardiovasc. Med. 3(5):163-170 (1993).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Yokoyama et al., *Characterization of physical entrapment and chemical conjugation of adriamycin in polymeric micelles and their design for in vivo delivery to a solid tumor*, Journal of Controlled Release 50:79-92 (1998).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine in Cardiovascular Health*, U.S. Pharmacist Continuing Education, printed Sep. 12, 2002.

* cited by examiner

IMPLANTABLE MEDICAL DEVICES INCORPORATING PLASMA POLYMERIZED FILM LAYERS AND CHARGED AMINO ACIDS

CROSS REFERENCE

This application is a divisional of application Ser. No. 10/176,506, filed Jun. 21, 2002, now U.S. Pat. No. 7,056,523 which is hereby incorporated herein by reference.

BACKGROUND OF THE INVENTION

1. Field of the Invention

This invention relates to the field of medical devices, such as stents. More particularly, this invention is directed to coatings which include chemically-bound polymers and/or oligomers of L-arginine.

2. Description of Related Art

In the field of medical technology, there is frequently a necessity to administer drugs locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results.

A commonly employed technique for the local delivery of a drug is through the use of a medicated stent. One method of medicating a stent is by coating the stent with a polymer having a drug incorporated therein. L-arginine, or polypeptide oligomeric derivatives thereof, for example, those containing 5 to 20 amino acid units, is one example of a substance that can be delivered via a stent.

L-arginine is known to be a precursor of endothelium derived nitric oxide (NO). NO is synthesized from L-arginine, or its polymeric and/or oligomeric derivatives, by the enzyme NO synthase oxygenase, a homodimeric flavo-hemoprotein that catalyzes the 5-electron oxidation of L-arginine to produce NO and L-citrulline. Among other therapeutic properties, NO relaxes vascular smooth muscle cells and inhibits their proliferation. References describing beneficial therapeutic properties of L-arginine include U.S. Pat. No. 5,861,168 to Cooke et al. Cooke et al. teach that administering L-arginine, as the NO precursor, restores vascular NO activity in patients with endothelial vasodilator dysfunction due to restenosis. Moreover, Uemura et al. (Circulation, vol. 102, 2629-2635 (2000)), teach that the heptamer of L-arginine (R7) exhibits biological activity in the reduction of neointimial hyperplasia.

According to traditional techniques, L-arginine or its polymers and/or oligomers can be physically incorporated into a polymeric matrix for in situ local delivery. The embodiments of the present invention provide alternative methods for local delivery of L-arginine, or its polymers and/or oligomers, by an implantable device such as a stent.

SUMMARY

An implantable medical device is provided, comprising a plasma polymerized film layer and a polypeptide chemically bonded to the plasma polymerized film layer. The device can be, for example, a stent, such as a balloon expandable or self-expandable stent. The plasma polymerized film layer can be derived from an organic substance having carboxyl groups. The organic substance can include a low molecular weight organic acid such as acrylic acid, propionic acid, butyric acid, valeric acid, and methacrylic acid. Representative examples of the polypeptide can include poly(L-arginine), poly(D-arginine), poly(L-lysine), poly(D-lysine), poly(δ-guanidino-α-aminobutyric acid), or a racemic mixture of poly(L-arginine) or poly(D-arginine). In accordance with one embodiment, a surface of the device on which the plasma polymerized film layer is deposited includes a carbon deposit, wherein the plasma polymerized film layer is formed over and is bonded to the carbon deposit.

A method of forming a coating for an implantable medical device is also provided, comprising forming a plasma polymerized film layer on the device and bonding a polypeptide to the plasma polymerized film layer. In one embodiment, the method can additionally include implanting carbon deposits in the surface of the device prior to forming the plasma polymerized film layer, wherein the plasma polymerized film layer is formed on carbon deposits. The bonding of the polypeptide to the plasma polymerized film layer can be conducted by exposing the plasma polymerized film layer to a free base form of the polypeptide.

A stent comprising a plasma polymerized film layer and an amino acid ionically bonded to the plasma polymerized film layer is also provided.

A method of treatment of a patient having a vascular occlusion is also provided, comprising implanting a stent at the site of the occlusion, the stent including a plasma polymerized film layer having a first charge and administering to the patient a polypeptide having an opposing second charge wherein some of the polypeptide circulating through the blood stream of the patient will couple to the plasma polymerized film layer. The polypeptide can be administered orally, intravenously, or by a drug delivery catheter.

DETAILED DESCRIPTION

L-arginine, commonly abbreviated as "R" or "Arg," also known as 2-amino-5-guanidinovaleric acid, has a formula $NH=C(NH_2)-NH-(CH_2)_3-CH(NH_2)-COOH$. L-arginine is an amino acid. Due to the presence of a strong basic guanidinium group, $-NH-C(NH_2)=NH$, carrying a partially uncompensated positive charge, L-arginine, its polymers and/or oligomers are highly cationic. For example, the heptamer of L-arginine has a $pK_a$ of 13.2.

Polymers and/or oligomers of L-arginine that can be used are referred to herein as "PArg." PArg are polycationic peptides comprising a plurality of repeating monomeric amino acid units and have a general formula $H-[NH-CHX-CO]_p-OH$, where "p" can be within a range of 5 and 1,000, typically, within a range of between 5 and 20. For example, a heptamer (designated R7) or a nonamer (R9), having p=7 and p=9, respectively, can be used. In the formula of PArg, "X" is 1-guanidinopropyl radical having the structure $-CH_2-CH_2-CH_2-NH-C(NH_2)=NH$. The terms "polymers and/or oligomers of L-arginine" and "PArg" are intended to include L-arginine in both its polymeric and oligomeric form.

In addition to PArg, other polycationic peptides can be alternatively used. Examples of such alternative polycationic peptides include poly(L-arginine), poly(D-arginine), poly(L-lysine), poly(D-lysine), poly(δ-guanidino-α-aminobutyric acid), racemic mixtures of poly(L-arginine) and poly(D-arginine), and chitosan.

The modification of the surface of the substrate, for example a surface of a stent, can include the following steps:
  (a) implanting of carbon into the stent surface;
  (b) functionalizing the stent surface containing the implanted carbon; and
  (c) neutralizing the functionalized stent surface.

Prior to the implantation of carbon, the outer surface of the stent can be cleaned by, for example, argon plasma treatment or any other suitable cleaning method so as to remove contaminants and impurities that are introduced during the manufacturing process. To implant carbon into the surface, in accordance with one method, the stent can be treated with methane plasma in a Plasma Ion Implantation Unit (PIIU). PIIU is a system known to those having ordinary skill in the art. The methane plasma treatment can be conducted by enclosing the stent inside a stainless steel mesh followed by generating the methane plasma using a radio frequency power source. The length of time needed implant the necessary amount of carbon into the stent surface can be between about 2 to 5 minutes. Process parameters for the methane plasma that can be employed are listed in Table 1 below.

TABLE 1

The Parameters of the Methane Plasma for Implantation of Carbon into the Stent Surface (>99.9% by Volume of Methane)

| Parameter | Parameter Range | Exemplary Value |
|---|---|---|
| Methane gas flow rate (sccm) | 10 to 200 | 30 |
| Volume of the PIIU chamber (cm$^3$) | — | 2,000 |
| Pressure (mTorr) | 0.1 to 2.0 | 0.5 |
| RF power (Watts) | 10 to 1,000 | 100 |
| RF frequency (MHz) | 2 to 2,800 | 13.56 |
| Bias voltage--stent (kV) | −10 to −80 | −50 |
| Pulse width--stent (μs) | 5 to 100 | 20 |
| Frequency--stent (Hz) | DC to 2,000 | 200 |

Alternatively, the stent can be implanted with carbon by sputtering carbon from a carbon cage electrode. The stent can be placed inside the carbon cage electrode, which in turn can be put inside a plasma chamber. A plasma, for example, argon plasma, can be generated using a radio frequency power source, followed by applying a bias voltage to the carbon cage. In addition to argon, the gaseous medium can also include other components such as nitrogen, for example, 1:1 by volume blend of argon and nitrogen. The length of time needed implant the necessary amount of carbon into the stent surface can be between about 2 to 5 minutes. Process parameters for the argon plasma that can be employed are listed in Table 2. Under the described conditions, carbon can be sputtered from the carbon cage, accelerated towards the stent surface, and implanted into the stent surface.

TABLE 2

The Parameters of the Argon Plasma for Implantation of Carbon into the Stent Surface by Sputtering Carbon from a Carbon Electrode (>99.9% by Volume of Argon)

| Parameter | Parameter Range | Exemplary Value |
|---|---|---|
| Gas flow rate (sccm) | 10 to 500 | 50 |
| Volume of the PIIU chamber (cm$^3$) | — | 2,000 |
| Pressure (mTorr) | 0.1 to 500 | 50 |
| RF power (Watts) | 10 to 1,000 | 200 |
| RF frequency (MHz) | 2 to 2,800 | 13.56 |
| Bias voltage--stent (kV) | −5 to −30 | −10 |
| Bias voltage-carbon electrode (kV) | 15 to 20 | 20 |
| Pulse width--stent (μs) | 5 to 20 | 20 |
| Frequency--stent (Hz) | DC-2,000 | 500 |
| Bias voltage-grid of the PIIU (V) | −300 to −5,000 | −1,000 |

Subsequent to the implantation of the carbon deposit, the stent can be cleaned using argon plasma. Process parameters for the argon plasma cleaning that can be employed are listed in Table 3.

TABLE 3

The Parameters of the Argon Plasma for Cleaning the Stent (>99.9% by Volume of Argon)

| Process | Parameter Range | Exemplary Value |
|---|---|---|
| Argon flow rate (sccm) | 10 to 250 | 250 |
| Pressure (mTorr) | 10 to 250 | 230 |
| RF power (W) | 50 to 450 | 400 |
| RF frequency (MHz) | 2 to 2800 | 13.54 |
| Time (minutes) | 3 to 30 | 5 |

After the stent surface is implanted with carbon and cleaned as described above, or by using any other acceptable method of carbon implantation and cleaning known to those having ordinary skill in the art, the stent surface can be functionalized by plasma polymerization as is understood by those having ordinary skill in the art. Regardless of which method is used for implanting carbon into the stent surface, carbon dioxide/acrylic acid plasma can be used for functionalization.

To functionalize, the carbon-implanted stent surface can be exposed to carbon dioxide/acrylic acid plasma to form an acrylate or acrylate-like polymer film layer on the surface of the stent. The carbon deposit on the surface of the stent provides a site at which covalent bonds can be formed with the plasma deposited acrylate or acrylate-like polymer film layer. One having ordinary skill in the art will recognize that some fragmentation of the acrylate can typically occur during the plasma polymerization process, resulting in an acrylate-like polymer layer of fragmented acrylate being formed on the carbon-implanted stent surface.

The plasma can be generated using a radio frequency power source under the conditions shown in Table 4. Instead of acrylic acid, those having ordinary skill in the art may select another low molecular weight saturated or unsaturated organic acid, for example, propionic acid, butyric acid, valeric acid, methacrylic acid, or mixtures thereof.

TABLE 4

The Conditions for Conducting Functionalization of the Stent Surface by Plasma Polymerization (CO$_2$/Acrylic Acid Plasma)

| Parameter | Parameter Range | Exemplary Value |
|---|---|---|
| Acrylic acid gas rate (ml/min) | 0.05-0.35 | 0.2 |
| Carbon dioxide gas flow rate (sccm) | 60-200 | 90 |
| Power (W) | 10-300 | 100 |
| Volume of the PIIU chamber (cm$^3$) | — | 2,000 |
| Pressure (mTorr) | 70 to 250 | 150 |
| RF power (Watts) | 50 to 250 | 100 |
| RF frequency (MHz) | 2 to 2,800 | 13.56 |

Carbon dioxide and acrylic acid can be pre-mixed by combining their respective streams flowing at rates shown in Table 4, and the combined stream can be fed into the PIIU chamber. Carbon dioxide can be supplied with acrylic acid to limit the rate of de-carboxylation which can occur with an organic acid in a plasma field. Acrylic acid can be vaporized prior to being combined with carbon dioxide. To vaporize acrylic acid, vacuum can be employed, for example, about 50 mTorr vacuum, and acrylic acid can be introduced by using, for example, a syringe pump.

In another embodiment, carbon dioxide and vaporized acrylic acid can be fed into the PIIU chamber as separate streams, at a flow rate for each respective stream as shown in Table 4.

The acrylic acid plasma can be applied for about 10 minutes, the time limit being dependent on the desired thickness of the acrylate or acrylate-like polymer film layer. The thickness of the plasma polymer film layer can be about 20 nm to about 500 nm, more narrowly about 70 nm to about 150 nm, for example, about 125 nm. In accordance with another embodiment, a pulsed plasma condition, as is understood by one of ordinary skilled in the art, can be employed for the deposition of polymer film layer. The process parameters are similar to those shown by Table 4, but for the power range being between about 60 W to about 450 W, for example, between about 250 W and about 350 W. For the implementation of pulsed plasma, the RF power can be pulsed at about 500 to 5,000 Hz, for example 1,000 Hz to about 1,250 Hz, using, for example, a square wave pulse sequence. The duty period, the time in which the power is on, can be between 15% and 100%, for example, 20% to 35%. With the use of pulsed plasma condition, the rate of de-carboxylation can be further limited.

Following deposition of the plasma-polymerized film layer, the plasma field can be purged with argon without an applied RF field to allow surface free radicals to be quenched by recombination prior to exposure to atmospheric oxygen. Table 5 provides parameters for this quenching process:

TABLE 5

The Conditions for Recombination of the Surface Free Radicals

| Process | Parameter Range | Exemplary Value |
|---|---|---|
| argon | — | (>99.9% by volume) |
| Gas flow rate (sccm) | 30 to 300 | 230 |
| Pressure (mTorr) | 50 to 500 | 250 |
| Time (minutes) | 2 to 10 | 3 |

Following plasma polymerization, the carboxylated stent surface can be neutralized. To neutralize, the stent can treated with a diluted alkaline solution, for example, sodium hydroxide solution. The duration of treatment can be about 30 minutes. Following the process of neutralization, the stent can be washed with de-ionized water to remove the residual sodium hydroxide solution.

The neutralization procedure described above completes the process of modification of the stent surface. At this point, PArg, for example, R7 can be incorporated onto the stent by ionic coordination. To incorporate R7, the stent can be placed in a container containing an excessive amount of aqueous solution of R7, for example, the R7 solution in a free base form.

To obtain R7 in a free base form, R7 can be dissolved in water and a strong alkali can be added, such as potassium hydroxide KOH, raising the pH of the R7 solution to about 13. In a strongly alkaline environment, the guanidinium fragments of R7 are de-protonated and R7 in a free base form can be obtained as a result. In the free base form, R7 is a cation having the positive charge mainly concentrated on the imino nitrogen of the guanidinium group of R7 (NH=fragments). Such cation for the purposes of this invention is designated as $R7^+$.

When the carboxylated stent surface containing neutralized polyanionic poly(acrylic acid)-like material is brought in contact with the aqueous solution of R7, the macromolecules of the poly(acrylic acid)-like material get solvated followed by charge separation, for example by dissociation, leading to the creation of carboxyl-anions as shown by reaction (I):

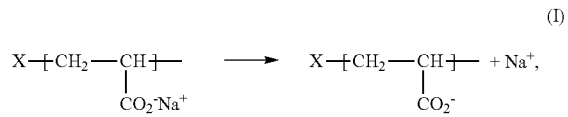

where X is a carbonized structure on the carbon-implanted stent surface to which poly(acrylic acid)-like material is attached.

$R7^+$ cations are then ionically coordinated around negatively charged carboxyl-anions. Such coordination can be schematically shown by reaction (II):

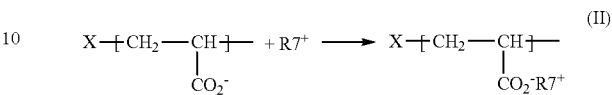

Alternatively, R7 in a non-free base form can be also coordinated around the carboxyl-anions. Although the cationic nature of R7 in the non-free base form is not as pronounced as it is in the free base form, the positive charge on the guanidinium group is sufficient to cause coordination of R7 around the carboxylated stent surface.

When the modified neutralized stent is brought in contact with the R7 solution, the solution can be gently agitated, for example, by stirring for about 30 minutes, followed by rinsing the stent with de-ionized water and drying. Optionally, a polymeric topcoat can be then applied, examples of suitable polymers being poly(ethylene-co-vinyl alcohol) and poly(butyl methacrylate).

According to another embodiment, when R7 is brought in contact with the neutralized modified stent surface containing carboxyl groups, R7 can be trapped by being grafted to the carboxyl groups-containing stent surface by covalent conjugation. The carboxyl groups will react with amino groups of R7 to form an amide. One possible path of reaction can be illustrated by reaction (III) and the conditions of the reaction will be selected by those having ordinary skill in the art:

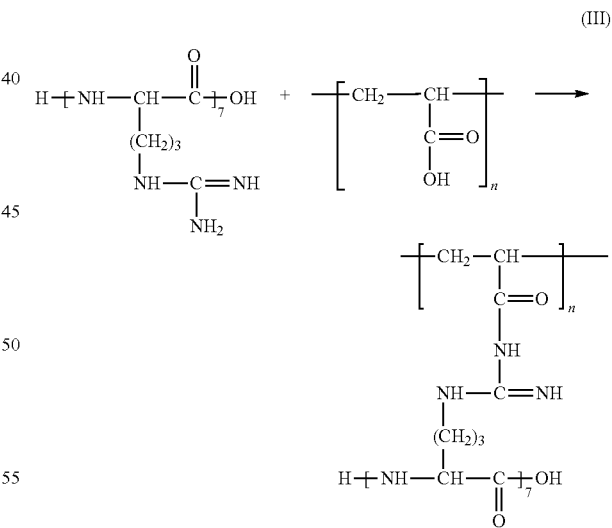

According to yet another embodiment, the stent, modified and neutralized as described above, can be placed at a diseased site in a blood vessel. Due to the polyanionic nature of the poly(acrylic acid) coating, the stent coating will carry a negative charge. R7 is then administered systemically, for example, intravenously, orally or through a perfusion balloon. R7 will be carried through the circulatory system and when R7 approaches the stent, some of positively charged R7 will coordinate around the negatively charged stent surface to form an ionic complex between R7⁺ and the poly(acrylic acid)-based anion, thus trapping R7. After untrapped R7 is cleared from the circulatory system, trapped R7 will still persist for some time providing an enhanced concentration of R7 at the vascular injury site.

The method of the present invention has been described in conjunction with a stent. The stent can be used in any part of the vascular system, including neurological, carotid, coronary, renal, aortic, iliac, femoral or any other peripheral vascular system. The stent can be balloon-expandable or self-expandable. There are no limitations on the size of the stent, its length, diameter, strut thickness or pattern.

The use of the coating is not limited to stents and the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a plasma polymerized film layer and a substance comprising a charged amino acid group, wherein the substance is attached to the plasma polymerized film layer,
    wherein the attachment comprises an ionic bond between the substance and the plasma polymerized film layer.

2. The stent of claim 1, wherein the substance comprises L-arginine, D-arginine, L-lysine, D-lysine, δ-guanidino-α-aminobutyric acid, or combinations thereof.

3. The stent of claim 1, wherein the amino acid group comprises a positive charge.

4. The stent of claim 1, wherein the amino acid group comprises a negative charge.

5. The stent of claim 1, wherein the substance comprises chitosan.

6. The stent of claim 1, wherein the substance comprises a drug.

7. The stent of claim 1, wherein the stent comprises a carbon deposit on the surface of the stent, and wherein the carbon deposit is attached to the plasma polymerized film layer.

8. A stent comprising a plasma polymerized film layer and a substance comprising an amino acid, wherein the substance is chemically bonded to the plasma polymerized film layer,
    wherein the plasma polymerized film layer is derived from an organic substance having a carboxyl group.

9. The stent of claim 8, wherein the organic substance comprises a low molecular weight organic acid or a combination of low molecular weight organic acids.

10. The stent of claim 9, wherein the organic substance comprises a component selected from a group consisting of acrylic acid, propionic acid, butyric acid, valeric acid, methacrylic acid, and combinations thereof.

11. The stent of claim 8, wherein the substance comprises L-arginine, D-arginine, L-lysine, D-lysine, δ-guanidino-α-aminobutyric acid, or a mixture thereof.

12. The stent of claim 11, wherein the L-arginine is releasable for local delivery in a patient.

13. The stent of claim 8, wherein a surface of the stent on which the plasma polymerized film layer is deposited includes a carbon deposit, wherein the plasma polymerized film layer is formed on and bonded to the carbon deposit.

* * * * *